United States Patent [19]

Gaston-Johansson

[11] Patent Number: 5,018,526

[45] Date of Patent: May 28, 1991

[54] APPARATUS AND METHOD FOR PROVIDING A MULTIDIMENSIONAL INDICATION OF PAIN

[76] Inventor: Fannie Gaston-Johansson, 1318 N. 127th Ave., Omaha, Nebr. 68154

[21] Appl. No.: 316,497

[22] Filed: Feb. 28, 1989

[51] Int. Cl.⁵ ............................................... A61B 5/00
[52] U.S. Cl. ..................................... 128/630; 128/897; 128/898
[58] Field of Search ................ 128/630, 897, 898, 744

[56] References Cited

U.S. PATENT DOCUMENTS 4,844,091 7/1989 Bellak .................................. 128/744

FOREIGN PATENT DOCUMENTS 2049431 12/1980 United Kingdom ................. 128/630

Primary Examiner—Max Hindenburg
Assistant Examiner—Randy Shay

[57] ABSTRACT

An instrument for providing a multidimensional indication of pain includes an elongated base having a series of sensory pain descriptors and emotional pain descriptors displayed thereon. A selection indicator next to each descriptor is adjustable by a person to indicate whether that descriptor accurately describes the pain the person is feeling. The descriptors may be assigned a numerical rank so that the total of the ranks of the selected descriptors affords a quantitative measurement of the sensory and emotional dimensions of a person's pain. A further cognitive dimension of the person's pain can be measured with an elongated pain scale on the instrument. This scale provides a visible indicia symbolizing the range of pain one can experience and a scale indicator slidable on the instrument to a selected position along the scale to indicate the intensity of pain being experienced by the person. A second quantitative scale cooperates with the same scale indicator to afford a ready quantitative reading corresponding to the selected position on the elongated pain scale.

20 Claims, 4 Drawing Sheets

APPARATUS AND METHOD FOR PROVIDING A MULTIDIMENSIONAL INDICATION OF PAIN

BACKGROUND OF THE INVENTION

The present invention is directed generally to a tool for providing a multidimensional indication of the pain being experienced by a person, and more particularly to a handheld tool having indicators thereon which may be adjusted by a person to provide a reliable and physical indication of the type and intensity of pain being experienced by a person.

When a person in need of medical treatment first contacts a doctor or a nurse, the person generally attempts to verbally describe his or her pain so that the medical personnel can make at least an initial diagnosis of the patient's condition and plan the appropriate treatment. This presents a significant problem for medical personnel, however, due to the fact that different people experience and, therefore, describe their pain or symptoms in different ways. One person may be stronger than another. A third person may have become accustomed to the ache after a period of time and, therefore, may describe the ache with milder words than he would have used if the ache had recently occurred. The changing expressions for pain which a diagnostician may hear complicates the quick and definite diagnosis of a person's illness or injury.

Devices for measuring pain have previously been proposed, such as that disclosed in United Kingdom Patent Application GB 2 049 431 A, which provides a sliding scale displaying a straight line with "no pain" indicated at one end and "intense pain" indicated at the other end of the line and an indicator slidable on the scale by a person to the position which corresponds proportionately to the pain felt by the person. But this device suffers from the same shortcoming as verbal communication in that it measures pain in only one dimension and based on the person's own very subjective assessment of what he feels.

Accordingly, there is a need for a simple device for providing a reliable assessment of the pain experienced by a person so that an accurate diagnosis may be made and early treatment begun.

A primary object of the invention, therefore, is to provide a simple yet effective instrument for providing a reliable multidimensional indication of the pain being experienced by a person.

Another object is to provide such an instrument which is readily adjusted by a person to record the pain experienced by him or her at that time.

Another object is to provide such a device which provides physical indicators of the pain experienced by a person so that its use does not require the assistance of another person to separately record the information and so that the indicated pain reading is preserved until the instrument is altered, reset or reused.

Another object is to provide such a device which affords the patient a visual indication of relative degrees of pain, yet simultaneously affords medical personnel or the person a definite quantitative measurement of the level of pain indicated by the person.

Another object is to provide such an instrument which is simple and rugged in construction, inexpensive to manufacture and efficient in operation.

SUMMARY OF THE INVENTION

The instrument of the invention, for providing a multidimensional indication of the pain being experienced by a person, includes an elongated base having a series of sensory pain descriptors and emotional pain descriptors displayed thereon. Next to each descriptor is a selection indicator which is adjustable by a person between a first state indicating that the associated descriptor describes the person's pain and a second state indicating that the associated descriptor does not describe the person's pain. Accordingly, a person need only adjust each sensor to the appropriate first or second state to afford a ready indication of both the sensory and emotional dimensions of pain experienced by the person.

The instrument, furthermore, may be provided with an elongated pain scale providing visible indicia symbolizing the range of pain one can experience and a scale indicator slidably supported on the base to a selected position along the scale to provide an indication of the cognitive dimension of pain experienced by the person. A second scale may be provided on the base, preferably out of view of the elongated pain scale, but at a position for cooperation with the scale indicator to provide a quantitative reading which is indicative of the adjusted position of the scale indicator on the elongated pain scale.

In accordance with the method of the invention, such an instrument is handed to a person who has been requested to adjust the various selection indicators to indicate whether each sensory and emotional pain descriptor accurately describes the pain that they feel. Similarly, the person is requested to adjust the sliding scale indicator to the position which most appropriately indicates the level of pain being experienced by the person. The adjusted instrument can then be examined immediately or at any later time to afford a multidimensional i.e., sensory, emotional and cognitive, indication of the pain experienced by the person at the time the instrument was used.

A numerical rank may be assigned to each descriptor so that the ranks of the sensory pain descriptors selected by a person can be added up to provide a quantitative measurement of the sensory dimension of the pain and the ranks of the emotional pain descriptors selected by the person can be added up to provide a quantitative measurement of the emotional dimension of the pain. This information, in combination with the quantitative cognitive reading from the second scale, enables a person to more accurately and reliably describe their pain and, therefore, assists medical personnel in making a more reliable diagnosis and effective treatment plan for the person.

DESCRIPTION OF THE PREFERRED EMBODIMENT

Figure 1:
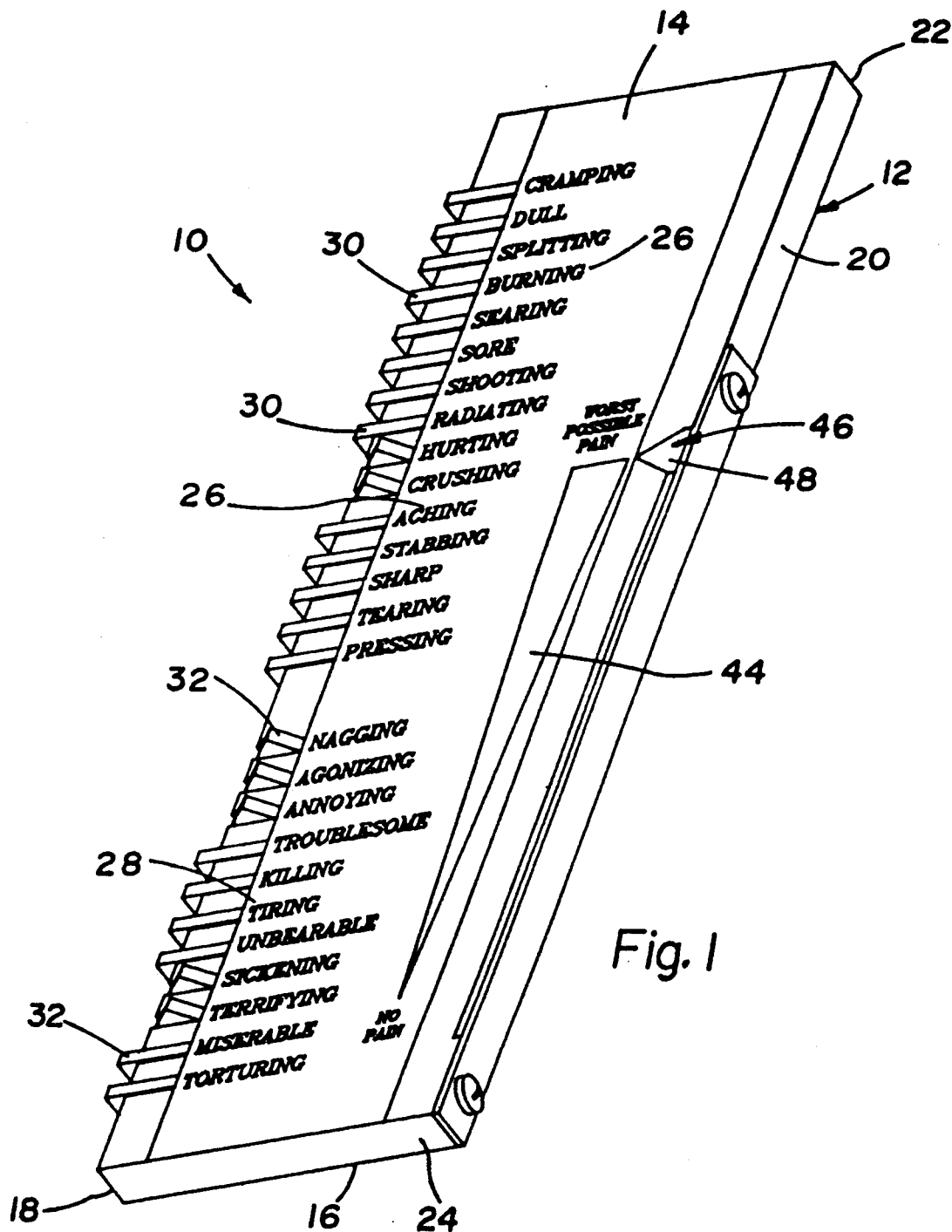
FIG. 1 is a perspective view of the pain measurement instrument of the invention.
Figure 2:
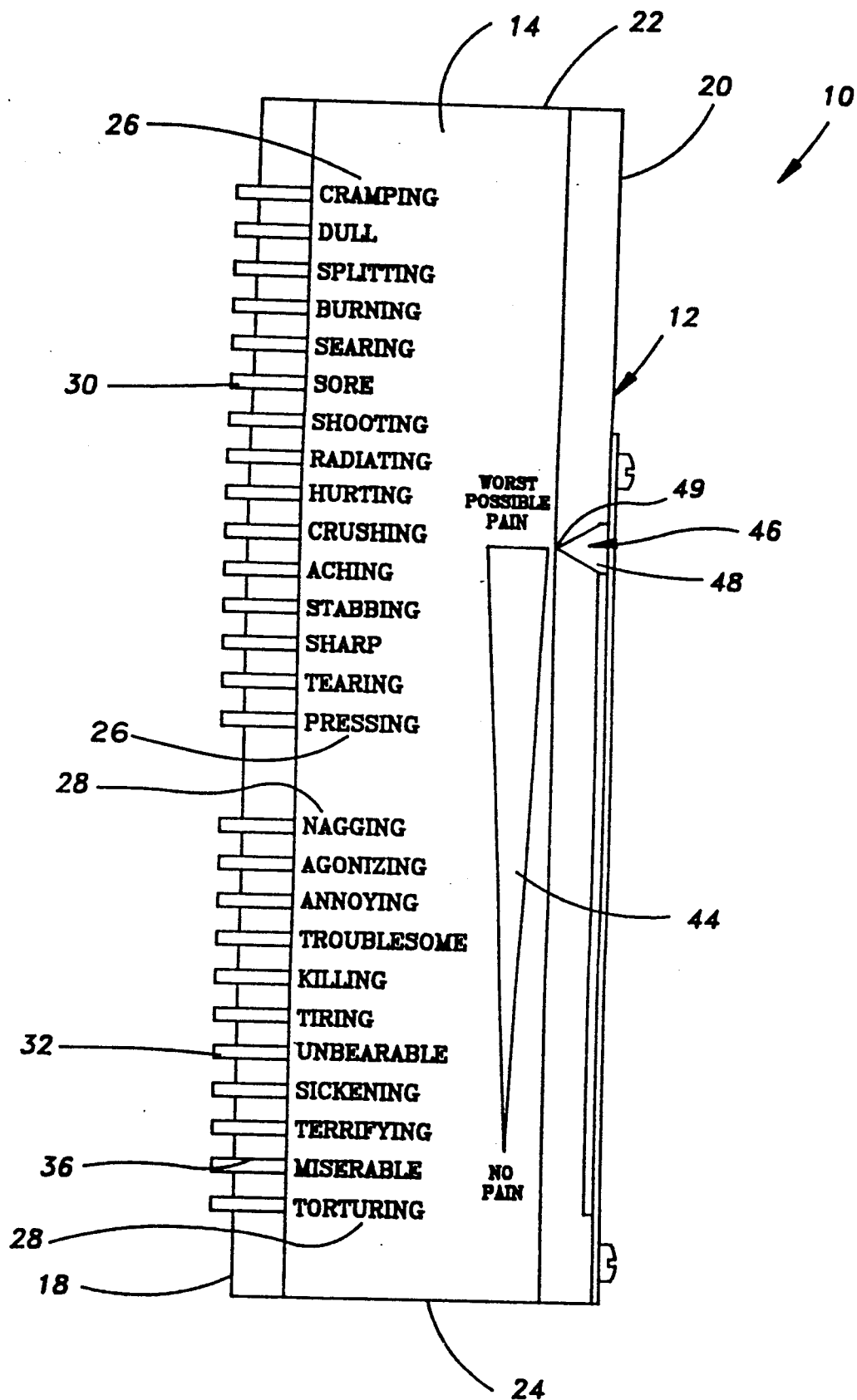
FIG. 2 is a top plan view of the pain measurement instrument.
Figure 3:
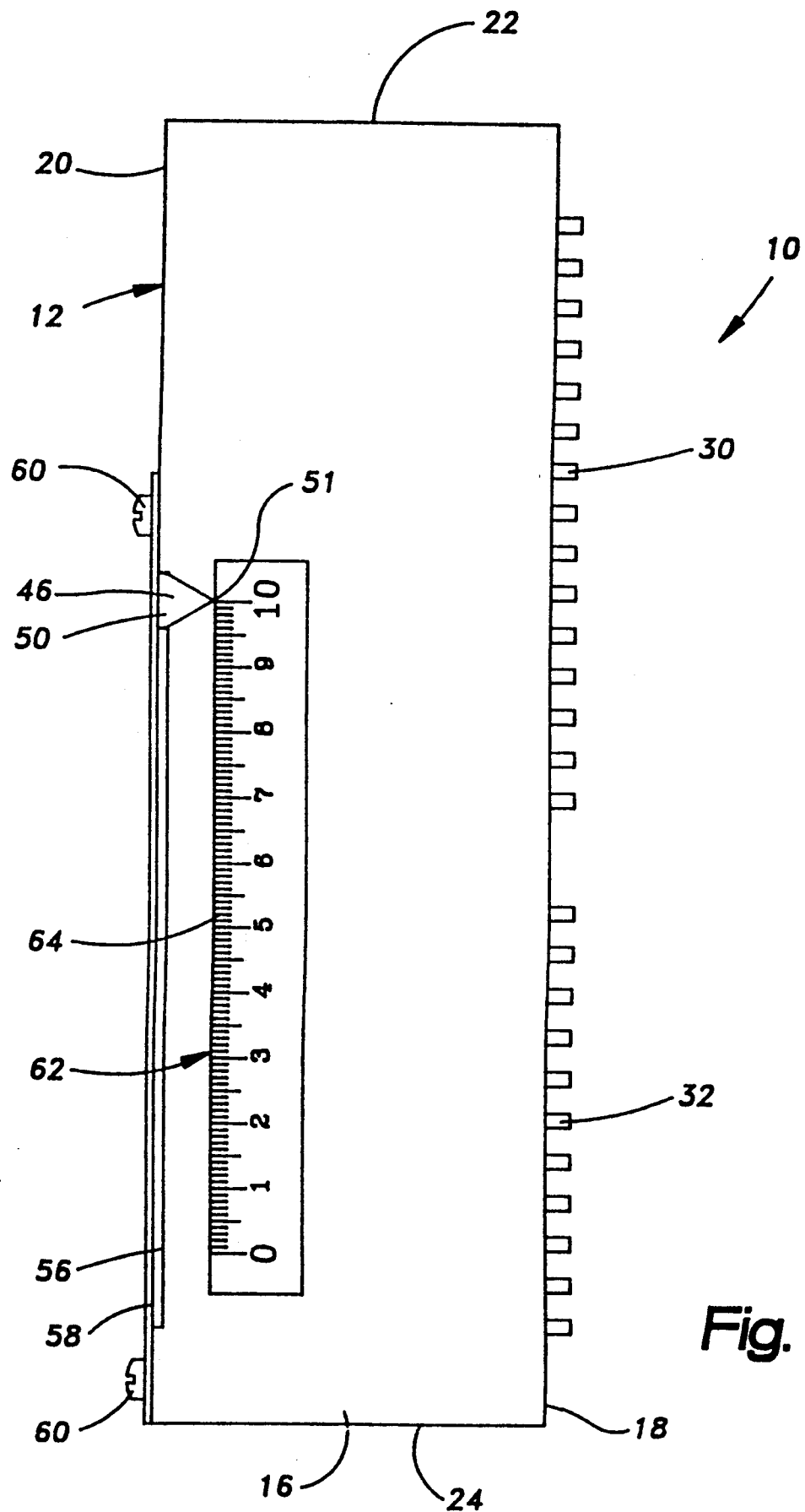
FIG. 3 is a bottom plan view of the pain measurement instrument.
Figure 4:
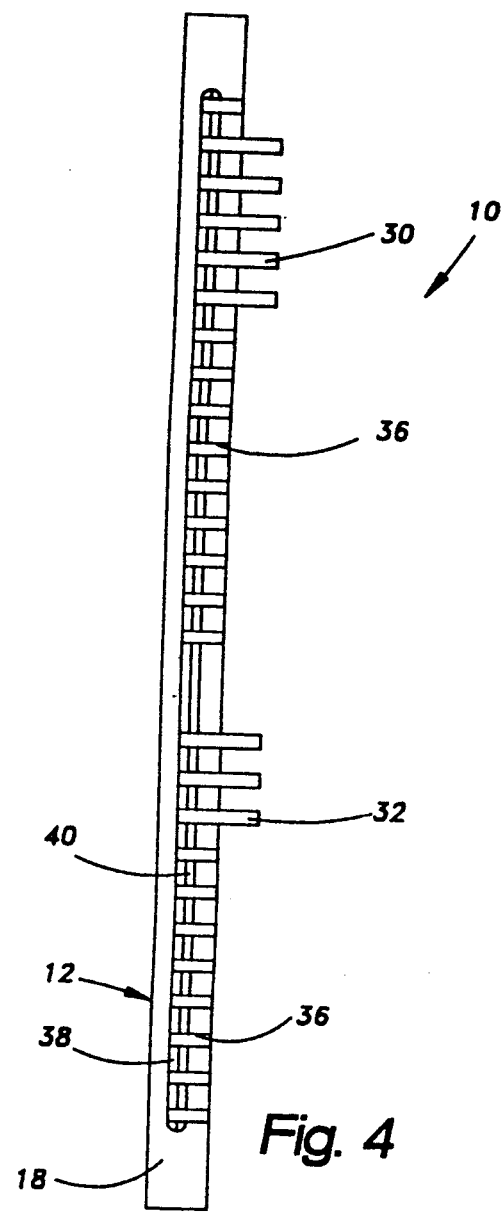
FIG. 4 is a side elevational view of the pain measurement instrument showing the selection indicators at different positions thereon.

The multidimensional pain measurement instrument 10 of the invention is illustrated in the drawings as including an elongated base 12 on which various indicators are provided to give measurements of the sensory, emotional and cognitive dimensions of pain being experienced by a person using the instrument.

Base 12 has generally flat opposite top and bottom surfaces 14 and 16, opposite side edges 18 and 20 and opposite ends 22 and 24. A list of sensory pain descriptors 26 are displayed in column format on an upper portion of top surface 14 adjacent to but spaced from edge 18. The sensory pain descriptors 26 are words describing various degrees and characteristics of the sensory dimension of experiencing pain. A numerical rank is assigned to each of the descriptors, as indicated in the following chart, but these rank numbers are not displayed on the instrument. The descriptors are preferably arranged in random order with respect to rank so that the order on the instrument does not correlate to the numerical rank. The purpose of the numerical rank is discussed hereinafter.

Below the sensory pain descriptors 26 on top surface 14, there is displayed the list of emotional pain descriptors 28, which are set forth in the following chart with their assigned rank:

|  | Rank |
| --- | --- |
| Sensory Pain Descriptor |  |
| Cramping | 4 |
| Dull | 1 |
| Splitting | 5 |
| Burning | 4 |
| Searing | 4 |
| Sore | 1 |
| Shooting | 5 |
| Radiating | 3 |
| Hurting | 2 |
| Crushing | 4 |
| Aching | 3 |
| Stabbing | 5 |
| Sharp | 5 |
| Tearing | 5 |
| Pressing | 2 |
| Emotional Pain Descriptor |  |
| Nagging | 1 |
| Agonizing | 4 |
| Annoying | 1 |
| Troublesome | 2 |
| Killing | 5 |
| Tiring | 3 |
| Unbearable | 5 |
| Sickening | 4 |
| Terrifying | 5 |
| Miserable | 3 |
| Torturing | 5 |

The emotional pain descriptors are words which define degrees or characteristics of the emotional dimension of experiencing pain.

The numerical ranks assigned to the descriptors constitute a pain rating index with "1" indicative of least pain and "5" indicative of most pain. A person's choice of words descriptive of their pain is calculated to determine pain intensity.

Two major indexes are obtained for the emotional, as well as the sensory components of pain:

(a) The number of words chosen (NWC), and (b) The pain rating index rank (PRIR), based on a summation of the numerical values assigned to the chosen words. Subjects are asked to choose from each group of descriptors those words which best describe their pain. The quality of pain is reflected in the specific words chosen by the subjects, and pain intensity is calculated on the basis of the number of words chosen and the pain rating index rank. Thus, this instrument allows pain to be analyzed both quantitatively and qualitatively.

Figure 5:
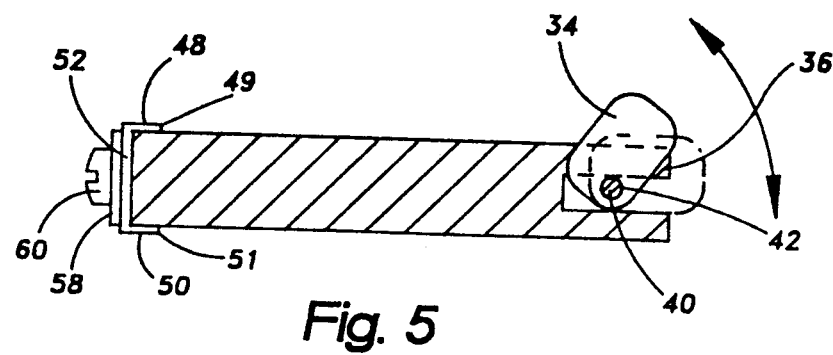
FIG. 5 is an enlarged end sectional view illustrating the adjusting positions of a selection indicator.

In order to physically indicate a person's choice of descriptors, base 12 includes a plurality of selection indicators 30 and 32 which are arranged in longitudinally spaced relation adjacent side edge 18 at positions aligned with and corresponding to the respective descriptors 26 and 28. Whereas the selection indicators may take many forms, the selection indicator 32 of the preferred embodiment is illustrated in FIG. 5 as including a toggle 34 inserted into a transverse slot 36 which communicates with a longitudinal extended channel 38 inside edge 18. A toggle retainer rod 40 extends through a hole 42 in each toggle 34 for pivotally supporting the toggle within its respective slot 36. All of the toggles are thus pivotal between the solid and dotted line raised and lowered positions indicated in FIG. 5. The raised solid line position preferably indicates a first state meaning that the associated descriptor accurately describes the person's pain. Leaving the toggle in the lowered dotted line position or second state indicates that the associated descriptor does not accurately describes the person's pain. The toggles are preferably freely pivotal on rod 40, but are frictionally engaged by the opposite sides of the respective transverse slot 36 to releasably retain the toggle in whichever position a person adjusts it to. The instrument may preferably be handed to a person with all toggles 34 arranged in the lowered second position so that the person can raise those toggles which accurately describe his or her pain.

A further cognitive dimension of the person's pain is provided by an elongated pain scale 44 which is also preferably displayed on top surface 14 adjacent a slidable scale indicator 46. The elongated pain scale 44 should provide a visual symbol indicative of increasing pain toward one end of the scale. For example, the preferred embodiment displays a tall thin upright triangle having two corners at the top end of the scale adjacent the words "worst possible pain" and one corner at the bottom end of the scale adjacent the words "no pain". The increasing thickness of the triangle from the bottom and toward the top end visually symbolizes the range of pain that can be experienced by a person. To indicate the level of pain a person is experiencing, he need only adjust the scale indicator longitudinally along pain scale 44 to the position where the proportional width of the triangular shaped scale corresponds to the level of pain being experienced by the person. The visual perception afforded by the triangular scale, therefore, helps a person select the longitudinal position most indicative of his pain.

In the end sectional view of FIG. 5, it is seen that the scale indicator 46, in the preferred embodiment, is a U-shaped member having a pair of legs 48 and 50 slidably engaging the top and bottom surfaces 14 and 16 of base 12 and a cross member 52 slidably engaging the side edge 20 of base 12. The portion of side edge 20 engaged by cross member 52 is recessed to form an elongated slot 56 so that a flat retention strip 58 may be secured to edge 20 by screw 60 for slidably retaining indicator 46 adjacent pain scale 44. Each leg 48 and 50 has a pointed end 49 and 51 for indicating a selected position on the associated scale. The ends of slot 56 are so arranged that the pointed end 49 of leg 48 is longitudinally moveable only along the longitudinal extent of the elongated pain scale 44.

The opposite leg 50 cooperates with a second quantitative scale 62, preferably on bottom surface 16 of base 12. The second scale has quantitative indicia, such as numbers 0 through 10 and corresponding divider lines 64 for designating positions between the whole numerals. Second scale 62 is arranged in spaced relation from edge 18 so that the pointed end 51 of leg 50 coincides with the edge of the scales for accurately reading a numerical designation corresponding to the adjusted position of the other leg 48 on elongated pain scale 44.

In operation, a multidimensional indication of the pain being experienced by a person can be obtained by providing the instrument of the invention to a person and causing him or her to adjust the selection indicators 30 and 32 to the positions indicating whether or not the associated descriptors are descriptive of the person's pain. The person is then requested or otherwise caused to slidably adjust the scale indicator 46 to a position on the pain scale 44 indicative of the extent of pain being experienced by the person.

To quantify the recorded pain for recordkeeping or comparison of the pain recorded at different times, a quantitative measurement of the cognitive dimension of the pain is readily available by simply observing the position of the pointed end 51 of scale indicator leg 50 on the second scale 62 on the back side of the instrument. A quantitative measurement of the sensory and emotional dimensions of the pain are obtained by adding up the ranks of the pain descriptors adjacent those selection indicators adjusted by the person to the first state, indicating that those descriptors are accurately descriptive of the patient's pain. The ranks of the selected sensory pain descriptors are added up separately from the ranks of the selected emotional pain descriptors as indicated in the following example.

| EXAMPLE: Person Chooses The Following Descriptors: | | | |
| --- | --- | --- | --- |
| Sensory Descriptors | Rank | Emotional Descriptors | Rank |
| Sharp | 5 | Agonizing | 4 |
| Aching | 3 | Troublesome | 2 |
| Burning | 4 | Annoying | 1 |
|  | 12 | Nagging | 1 |
|  |  |  | 8 |
| Pain Intensity Scores | | | |
| Sensory | 12 | | |
| Emotional | 8 | | |
| Total | 20 | | |

The above is one example of how scores are calculated and analyzed on the instrument of the invention. In this example, the sensory pain is more intense than the emotional pain. Accordingly, a physician would choose a treatment or medication that would be directed at reducing the sensory component of pain. For a woman experiencing labor pain, for example, the physician's choice of medication might be epidural anesthesia rather than valium, a drug directed at reducing the emotional component of pain. In comparison, a patient who has cancer may choose fewer and less intense sensory words than emotional words to represent pain intensity. This patient would be treated differently and the treatment would be directed at reducing the emotional component of pain, i.e., staying with the patient, giving information about what to expect, relaxation exercises, self-coping statements, tranquilizers, etc.

This instrument will be useful in hospitals, doctors offices, nursing homes and even in a home medicine cabinet where a person could use the instrument to effectively communicate his or her pain by telephone to a physician or other medical personnel. It has been found that reliable readings are obtainable from anyone over the age of 8 or 9.

A particular advantage is that the use of the device does not require a second person to be present to record descriptors selected by the persons since the instrument itself affords the physical indicators for recording right on the instrument which descriptors are selected. This eliminates the possibility of human errors in recording the information and also affords a way of preserving the person's selections for later review, observation or recording.

Whereas the invention has been shown and described in connection with a preferred embodiment thereof, it is apparent that many modifications, substitutions and additions may be made which are within the intended broad scope of the appended claims. Whereas styrene plastic is a preferred material for the base 12, it could alternately be made of stainless steel. Whereas the size of the preferred embodiment may be approximately two and a half inches by eight inches by seven sixteenth inches, ($2\frac{1}{2}'' \times 8'' \times 7/16''$) smaller and larger versions may be made. The descriptors and triangle indicia of the various scales are preferably inscribed into the base so that they will not be easily worn off. Larger instruments with larger letters may be more suitable for older patients and those with vision problems.

The instrument is not only useful for communicating pain in the first encounter with a physician, but may also be used for selecting and evaluating post operative treatment, both for choosing medication and determining the effect of the medication. Furthermore, the instrument is useful for measuring the efficacy of lowering pain by various treatments such as medication, acupuncture, hypnosis, analgesia and bio feedback among others.

Thus there has been shown and described an apparatus and method for providing a multidimensional indication of pain, which apparatus and method accomplish at least all of the stated objects.

I claim:

1. An apparatus for providing a multidimensional indication of the pain being experienced by a person, comprising, an elongated base having a plurality of sensory pain descriptors displayed thereon and a plurality of emotional pain descriptors displayed thereon, a selection indicator operatively associated with each descriptor, each selection indicator being on said base and selectively adjustable by a person between a first state indicating that the associated descriptor describes the person's pain and a second state indicating that the associated descriptor does not describe the person's pain.

2. The apparatus of claim 1 wherein said elongated base has generally flat opposite top and bottom surfaces and opposite side edges, said sensory pain descriptors and emotional pain descriptors all being displayed on said top surface of the base.

3. The apparatus of claim 2 wherein said sensory pain descriptors and emotional pain descriptors are arranged on said top surface in longitudinally spaced apart relation and said selection indicators are arranged in longitudinally spaced relation adjacent one side edge at positions corresponding to said descriptors.

4. The apparatus of claim 3 wherein a selection indicator includes a toggle supported on said base for pivotal movement between a first position corresponding to said first state and a second position corresponding to said second state.

5. The apparatus of claim 1 wherein said base further displays an elongated pain scale indicative of increasing pain toward one end of the scale, and
a scale indicator slidably supported on said base in association with said scale, said scale indicator being slidably adjustable on said base between positions indicative of worst possible pain at one end of said scale and no pain at the other end of said scale or the relative extent of pain corresponding to any position therebetween, thereby to provide a cognitive dimension to the pain measured by said apparatus.

6. The apparatus of claim 5, further comprising,
a second scale on said base and having opposite ends and quantitative indicia arranged on said second scale and extending between said opposite ends,
said scale indicator being operative to indicate a quantitative reading on said second scale which is indicative of the adjusted position of said scale indicator on said elongated pain scale.

7. The apparatus of claim 5 wherein said elongated pain scale displays a generally long thin triangular indicia having two corners at said one end of the scale and one corner at said other end of the scale and two sides diverging apart from said other end toward said one end.

8. The apparatus of claim 6 wherein said elongated base has generally flat opposite top and bottom surfaces and opposite side edges, said sensory pain descriptors and emotional pain descriptors all being displayed on said top surface of the base.

9. The apparatus of claim 8 wherein said second scale is arranged on the bottom surface of said base at a position out of sight to a person observing the pain scale on the top surface of the base.

10. The apparatus of claim 9 wherein said scale indicator comprises a generally U-shaped indicator having a pair of legs slidably engaging said top and bottom surfaces and a cross member slidably engaging one side edge of the base, each leg including means for indicating a selected position on the associated scale and means for releaseably retaining said scale indicator on said base.

11. The apparatus of claim 10, wherein said means for releaseably retaining said scale indicator on said base comprises an elongated slot along one side edge in which the cross member is slidably moveable and a generally flat retention strip secured to said side edge over said slot to retain said scale indicator between said base and retention strip.

12. The apparatus of claim 10, wherein said means for indicating a selected position on the associated scale comprises a pointed end of each leg.

13. An apparatus for providing a multidimensional indication of the pain being experienced by a person, comprising,
an elongated base having a plurality of sensory pain descriptors displayed thereon and a plurality of emotional pain descriptors displayed thereon,
a selection indicator operatively associated with each descriptor, each selection indicator being on said base and selectively adjustable by a person between a first state indicating that the associated descriptor describes the person's pain and a second state indicating that the associated descriptor does not describe the person's pain.
said base further displaying an elongated pain scale having opposite ends indicative of worst possible pain at one end and no pain at the other end, and
a scale indicator slidably supported on said base in association with said scale, said scale indicator being slidably adjustable on said base between positions indicative of worst possible pain at one end of said scale and no pain at said other end of said scale and the proportional extent of pain corresponding to any position therebetween thereby to provide a cognitive dimension to the pain measured by said apparatus,
a second scale on said base and having opposite ends and quantitative indicia arranged on said second scale and extending between said opposite ends,
said scale indicator being operative to indicate a quantitative reading on said second scale which is indicative of the adjusted position of said scale indicator on said elongated pain scale.

14. The apparatus of claim 13 wherein said elongated base has generally flat opposite top and bottom surfaces and opposite side edges, said sensory pain descriptors and emotional pain descriptors all being displayed on said top surface of the base.

15. The apparatus of claim 14 wherein said second scale is arranged on the bottom surface of said base at a position out of sight to a person observing the pain scale on the top surface of the base.

16. A method for providing a multidimensional indication of pain being experienced by a person, comprising
providing a tool having a plurality of sensory pain descriptors and a plurality of emotional pain descriptors displayed thereon, a selection indicator operatively associated with each descriptor and adjustable to first and second states indicating that the associated descriptor is descriptive and nondescriptive respectively, and
causing a person to adjust said selection indicators to said first and second states as indications of whether the associated descriptors are descriptive of the pain being experienced by the person.

17. The method of claim 16 further comprising assigning a numerical rank to each descriptor and further comprising adding up the ranks of the sensory pain descriptors adjacent those selection indicators adjusted by the person to the first state and adding up the ranks of the emotional pain descriptors adjacent the selection indicators adjusted by the person to the first state, thereby to provide quantitative measurements of the sensory and emotional pain experienced by the person.

18. A method for providing a multidimensional indication of pain being experienced by a person, comprising providing a tool having a plurality of sensory pain descriptors and a plurality of emotional pain descriptors displayed thereon, a selection indicator operatively associated with each descriptor and adjustable to first and second states indicating that the associated descriptor is descriptive and nondescriptive respectively, an elongated pain scale and a scale indicator slidably adjustable on said tool and operative in association with said scale to provide a cognitive measurement of pain, and a second quantitative scale associated with said scale indicator to provide a quantitative measurement of the extent of pain indicated by said scale indicator, causing a person to adjust said selection indicators to said first and second states as indications of whether the associated descriptors are descriptive of the pain being experienced by the person, causing a person to slidably adjust the scale indicator to a position on said pain scale indicative of the extent of pain being experienced by the person, and observing the quantitative measurement of pain indicated by the adjusted scale indicator on said second quantitative scale.

19. The method of claim 18 further comprising assigning a numerical rank to each descriptor and further comprising adding up the ranks of the sensory pain descriptors adjacent those selection indicators adjusted by the person to the first state, adding up the ranks of the emotional pain descriptors adjacent the selection indicators adjusted by the person to the first state, thereby to provide quantitative measurements of the sensory and emotional pain experienced by the person.

20. The method of claim 19 wherein said tool is a handheld tool and further comprising handing said tool to the person.

* * * * *